US 7,356,163 B2

(12) United States Patent
Beckert et al.

(10) Patent No.: US 7,356,163 B2
(45) Date of Patent: Apr. 8, 2008

(54) POSTAL IMAGE AUGMENTED BIO-WARFARE AEROSOLIZED AGENT TRIGGER

(75) Inventors: John T. Beckert, Winter Springs, FL (US); William C. Craig, Endwell, NY (US); Joan M. Marsh, Endwell, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 729 days.

(21) Appl. No.: 10/865,063

(22) Filed: Jun. 10, 2004

(65) Prior Publication Data

US 2005/0278142 A1    Dec. 15, 2005

(51) Int. Cl.
*G06K 9/00* (2006.01)
*G07C 5/00* (2006.01)

(52) U.S. Cl. .................... 382/101; 209/584
(58) Field of Classification Search .............. None
See application file for complete search history.

(56) References Cited

U.S. PATENT DOCUMENTS

| | | | |
|---|---|---|---|
| 4,775,246 A | 10/1988 | Edelmann et al. | 380/23 |
| 5,119,306 A | 6/1992 | Metelits et al. | 364/464.02 |
| 5,307,423 A | 4/1994 | Gupta et al. | 382/11 |
| 5,535,127 A | 7/1996 | Uno et al. | 364/464.02 |
| 5,737,438 A | 4/1998 | Zlotnick et al. | 382/101 |
| 5,754,671 A | 5/1998 | Higgins et al. | 382/101 |
| 5,805,710 A | 9/1998 | Higgins et al. | 382/101 |
| 5,862,243 A | 1/1999 | Baker et al. | 382/101 |
| 5,974,147 A | 10/1999 | Cordery et al. | 380/25 |
| 6,014,450 A | 1/2000 | Heilper et al. | 382/101 |
| 6,058,190 A | 5/2000 | Cordery et al. | 380/51 |
| 6,205,373 B1 | 3/2001 | Hart et al. | 700/222 |
| 6,289,109 B1 | 9/2001 | Gocht et al. | 382/101 |
| 6,327,373 B1 | 12/2001 | Yura | 382/101 |
| 6,363,484 B1 | 3/2002 | Cordery et al. | 713/182 |
| 6,373,973 B2 | 4/2002 | Neri et al. | 382/135 |
| 6,457,642 B1 | 10/2002 | Good et al. | 235/462.01 |
| 6,671,577 B2 * | 12/2003 | Barnum et al. | 700/223 |
| 7,024,019 B2 * | 4/2006 | Sansone | 382/101 |
| 2002/0106107 A1 | 8/2002 | MacDonald | 382/101 |
| 2002/0124664 A1 | 9/2002 | Call et al. | 73/863.22 |
| 2002/0126008 A1 | 9/2002 | Lopez et al. | 340/540 |
| 2002/0141613 A1 | 10/2002 | Sansone | 382/101 |
| 2005/0070025 A1 * | 3/2005 | Mooradian et al. | 436/178 |
| 2005/0243307 A1 * | 11/2005 | Silcott et al. | 356/73 |

* cited by examiner

*Primary Examiner*—Jingge Wu
*Assistant Examiner*—Charles Kim
(74) *Attorney, Agent, or Firm*—Burns & Levinson LLP; Jacob N. Erlich; Harvey Kaye

(57) ABSTRACT

A method and apparatus for reliably detecting bio-warfare agents in the mail stream that may be released from posted items. The agents are detected as the mail pieces are being processed using typical postal automation machines equipped with image scanning capabilities, and two technologies are combined.

One is an aerosol trigger that can be based on a variety of different existing approaches which detects particulates of a specific size range and examines the spectral characteristics of the particles when illuminated with an ultra violet (UV) or other light source. Other approaches may include: mass spectrometry, ion mobility, IR spectrometry and the like. The second technology involves scanning and analyzing images of suspect mail, pieces and correlating aerosol trigger events with mail piece image risk factors.

The second technology provides for obtaining images which provide information indicative of mail which is more likely to be from suspicious sources and provide increased risk factors.

20 Claims, 4 Drawing Sheets

POSTAL IMAGE AUGMENTED BIO-WARFARE AEROSOLIZED AGENT TRIGGER

CROSS-REFERENCE TO RELATED APPLICATIONS

The present application is related to an application entitled Chemical/biological Hazard Trigger With automatic Mail Piece Tagging System and Method, being filed on the same date as the present application, and having one common inventor, and the content thereof is hereby incorporated herein by reference.

BACKGROUND OF THE INVENTION

The present invention relates to a system and method for detecting hazardous materials on or inside articles and, more particularly, to a system and method for detecting hazardous materials on or in mail, by using two different detection methods, one for detecting hazardous materials and the other for recognizing mail with suspicious indicia on the envelope or other mail wrapper.

All economies depend upon the physical shipment of materials for their functioning including the shipment of mail, merchandise, raw materials, and other goods.

In some circumstances, it is desirable to subject the goods to some type of inspection to determine the presence of hazardous or impermissible materials, including biological and chemical materials. In general, sophisticated sensing systems are known for the detection of hazardous biological and chemical materials. For example, such systems can include conventional laboratory facilities as well as mobile or semi-mobile units that can automatically or semi-automatically detect the presence of the undesired substance or substances. Others include sensor or detectors for hazardous chemicals, explosives, illicit drugs, radioactive particles, and other hazardous materials. These sensors can be used single, or in combinations, to detect as many types of hazardous particles or vapors as required. It is desirable to have an accurate system for detection to reduce the number of false positives, the latter causing needless expense in the processing of the mail.

U.S. Pat. No. 4,775,246 for a system for detecting unaccounted for printing in a value printing system is for detecting fraudulent imprints on documents.

U.S. Pat. No. 5,119,306 for a mail piece weight quality control system and method discloses a system for certifying the accuracy of postage payments based on the weight of mail pieces.

U.S. Pat. No. 5,307,423 for a machine recognition of handwritten character strings such as postal zip codes or dollar amount on bank checks which discloses a system for recognizing a string of handwritten characters automatically using a graphic input.

U.S. Pat. No. 5,535,127 for a processing apparatus for mail with stamps discloses an automatic mail processing apparatus for detecting physical quantities of mail with a stamp and determining whether the postage is valid for the weight of the mail piece.

U.S. Pat. No. 5,737,438 for image processing discloses image processing apparatus for locating labels on images of parcels.

U.S. Pat. No. 5,754,671 for a method for improving cursive address recognition in mail pieces using adaptive data base management discloses such method using adaptive dictionary management which includes creating a number of word databases having the most frequently observed words in a particular portion of an address block derived from training data. Word images are compared to the database contents.

U.S. Pat. No. 5,805,710 for a method an system for adaptively recognizing cursive addresses on mail pieces and is similar to the '671 patent discussed above.

U.S. Pat. No. 5,862,243 for a system for evaluating bar code quality on mail pieces discloses a system which includes an imaging device providing an image of a barcode or address and also detects barcode defects.

U.S. Pat. No. 5,974,147 for a method of verifying unreadable indicia for an information-based indicia program discloses such a method includes attempting to read a 2-D barcode using sophisticated digital image processing when the bar code is not readable and then using two independent processes to determine the correct information.

U.S. Pat. No. 6,014,450 for a method and apparatus for address block location discloses a system for locating address indicia on digitized images of mail pieces for real time operation on computers.

U.S. Pat. No. 6,058,190 for method and system for automatic recognition of digital indicia images deliberately distorted to be non readable discloses an arrangement in which mail pieces are scanned and information is obtained about the printed data which information is processed to determine if it is readable, and if non readable an attempt is made to determine the cause of the non readability.

U.S. Pat. No. 6,205,373 for a method and system for tracking manually repaired mail pieces and the like discloses producing control documents with a data processing system and the mail piece are assembled in accordance with mail piece records identified by coded information on the documents and if a damaged mail piece is manually repaired and operator scans the coded information from the damaged mail piece.

U.S. Pat. No. 6,289,109 for a method and apparatus for processing mail pieces including means for identifying the location and content of data blocks thereon discloses apparatus for obtaining a digital bit map image of an outer surface of a mail piece to determine the type of data contained in the block.

U.S. Pat. No. 6,327,373 for a mail address reading apparatus and mail sorting apparatus discloses apparatus for determining a destination line when a zip code is not obtained at a likely location.

U.S. Pat. No. 6,363,484 discloses a method of verifying unreadable indicia for an information based indicia program and is related to the '147 patent discussed above.

U.S. Pat. No. 6,373,973 discloses a method and device for controlling valuable or security items such as banknotes.

U.S. Pat. No. 6,457,642 for an automated system and method for identifying and measuring packages transported through a laser scanning tunnel discloses the reading of bar codes while information is obtain about the package and mathematical models are used to in such a manner as to enable simultaneous tracking of multiple packages being transported through the scanning tunnel.

U.S. Published Application No. US 2002/0106107 published Aug. 8, 2002 if for a machine vision system and triggering method in which a video camera is used to continuously obtain video images of features of interest and the images are compared to a signature image and when there is a match the camera is triggered to acquire a full frame image containing the feature of interest.

U.S. Published Application No. US 2002/0126008 published Sep. 12, 2002 discloses use of sensors at various locations within a typical mail processing system to sense the presence of a harmful agent.

U.S. Published Application No. US 2002/0124664 shows a mail processing system which includes the screening of mail for contamination by biological or chemical agents.

U.S. Published Application 2002/0141613 published Oct. 3, 2002 is for a method for determining if mail contains life harming materials. Mail pieces are scanned for analysis for possible threat based on: (1) whether the overall image of the mail piece is similar to previous ones known to be harmful, but no details are provided as to how this is accomplished; (2) whether the addressee is known to be at high-risk of receiving dangerous mail pieces; and (3) whether the person mailing the piece in known to send dangerous material through the mail.

However, this criteria is unlikely to locate mail sent by persons who may be sending hazardous material through mail systems.

Some prior attempts to solve the problem of locating hazardous materials sent through the mails use DNA amplification technique—Polymerase Chain Reaction (PCR)—based on a one hour sample collection time with 40-60 minute processing window. The test is very expensive and relatively slow.

SUMMARY OF THE INVENTION

The present invention is arranged to reliably detect biowarfare agents in the mail stream that may be released from posted items. The agents are detected as the mail pieces are being processed using typical postal automation machines equipped with image scanning capabilities.

The detection problem is solved combining two technologies. The first technology is an aerosol trigger that can be based on a variety of different existing approaches. One such approach detects particulates of a specific size range and examines the spectral characteristics of the particles when illuminated with an ultra violet (UV) or other light source. Other approaches may include: mass spectrometry, ion mobility, IR spectrometry and the like. The second technology involves scanning and analyzing images of suspect mail pieces and correlating aerosol trigger events with mail piece image risk factors.

The second technology provides for obtaining images which provide information indicative of mail which is more likely to be from suspicious sources and provide increased risk factors such as the following:

a. Excessive postage;
b. Badly typed or hand written address;
c. Hand written characters are printed rather than script;
d. Typed address has uneven background of different color/shade (cut from other paper);
e. Misspelled words in address;
f. Addressed without any indicated name;
g. Excessive tape or discoloration evident in mail piece image;
h. No return address present;
i. Return address does not match postmark;
j. Return address is from a suspect area or interest; and
k. Various restrictive legends, such as: "Personal", "To be Opened Only by Addressee", "Special Delivery", "Open Immediately" and the like.

Aerosol trigger based systems have been tried on postal equipment in the past with mixed results due to false alarms. The addition of the image risk factors will improve the reliability of the trigger system resulting in fewer false alarms.

The present invention combines multi-spectral UV particle detector (or similar real time/near real time trigger technology) with mail piece image processing to improve accuracy of detection.

A combination of multi-spectral UV particle detection and mail piece image analysis is used to improve the accuracy of detection. providing greater accuracy and improved response time.

The present invention is arranged to work in conjunction with a chemical or biological hazard detection trigger attached to postal mail handling equipment. The invention provides a detection system where samples of air are tested, and, at a later stage the outside of the mail is scanned to provide images thereof, and the mail piece image data is correlated with the trigger data to determine the threat.

Work has been done with various aerosol particle detection equipment in an effort to develop a system for detecting aerosolized pathogens that may be emitted from mail pieces during processing. The present invention is for an arrangement in which, in addition, the markings on the mail are scanned to determine the level of threat, which is then correlated with the hazardous material detection.

This invention can work with any type of real time or near real time trigger mechanism—ultraviolet, mass-spectrometry, laser induced breakdown spectrometry and the like.

There is presently no automatic means for providing a sufficiently high level of confidence when hazardous material is detected.

The present invention combines real time trigger technology with high speed image scanning. The image scanning provides a means to rapidly identify mail pieces being processed at the time of the trigger event and correlating the mail piece to trigger parameters preserving the chain of evidence. The hazardous material detectors can be used to uniquely divert mail pieces that are identified as potentially hot for off-line second tier analysis.

Currently there is no direct means of identifying mail pieces being processed at the time of a trigger event. Off-line analysis of tag—ids (serial numbers) printed on the letters is currently required, which is time consuming and impractical.

Other features and advantages will be apparent from the following detailed description of preferred embodiments taken in conjunction with the accompanying drawings.

DESCRIPTION OF THE PREFERRED EMBODIMENTS OF THE INVENTION

Figure 1:
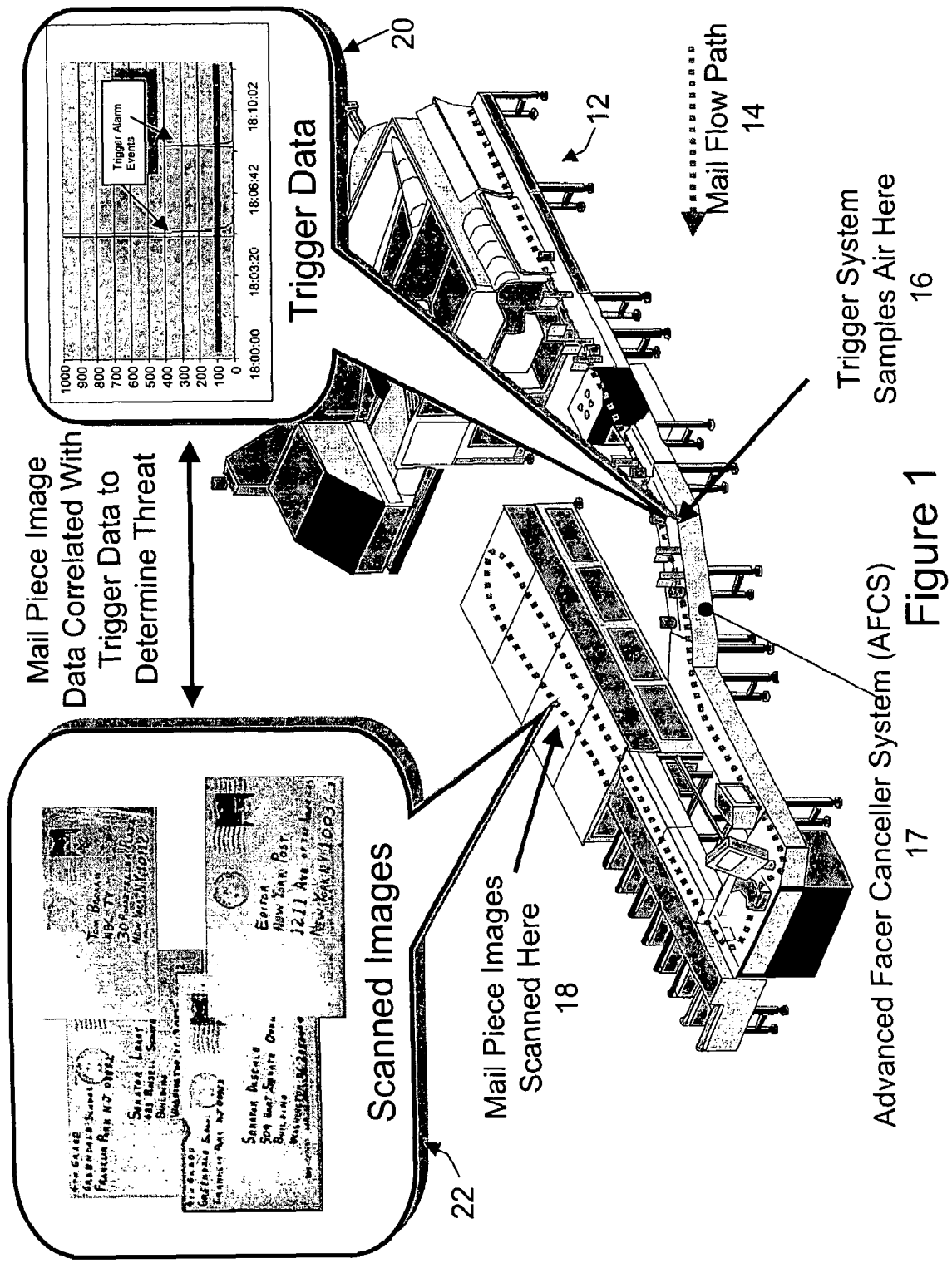
FIG. 1 is a schematic block diagram of the components of the system of the present invention.
Figure 2:
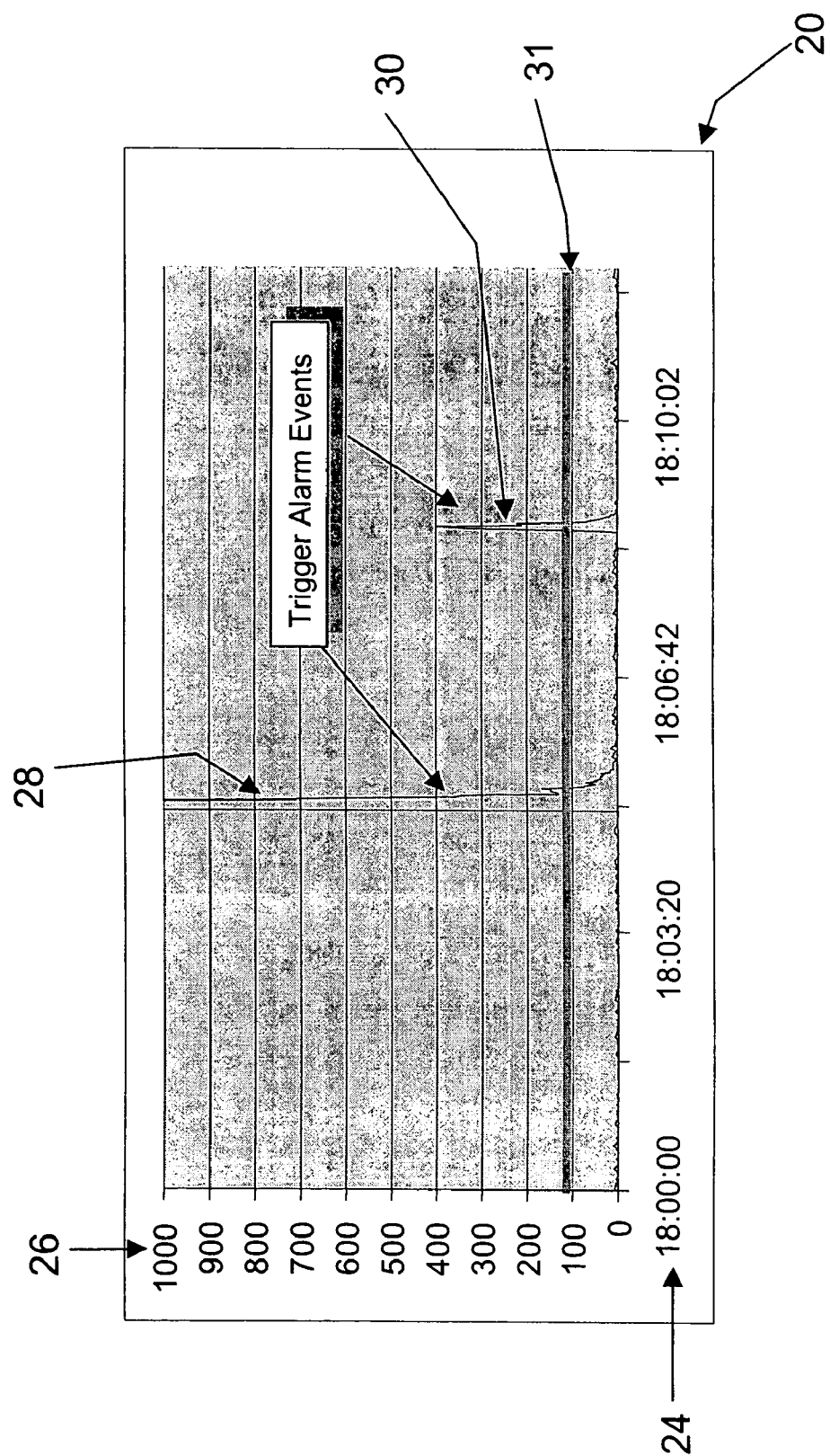
FIG. 2 shows a graph of the trigger alarm events.
Figure 3:
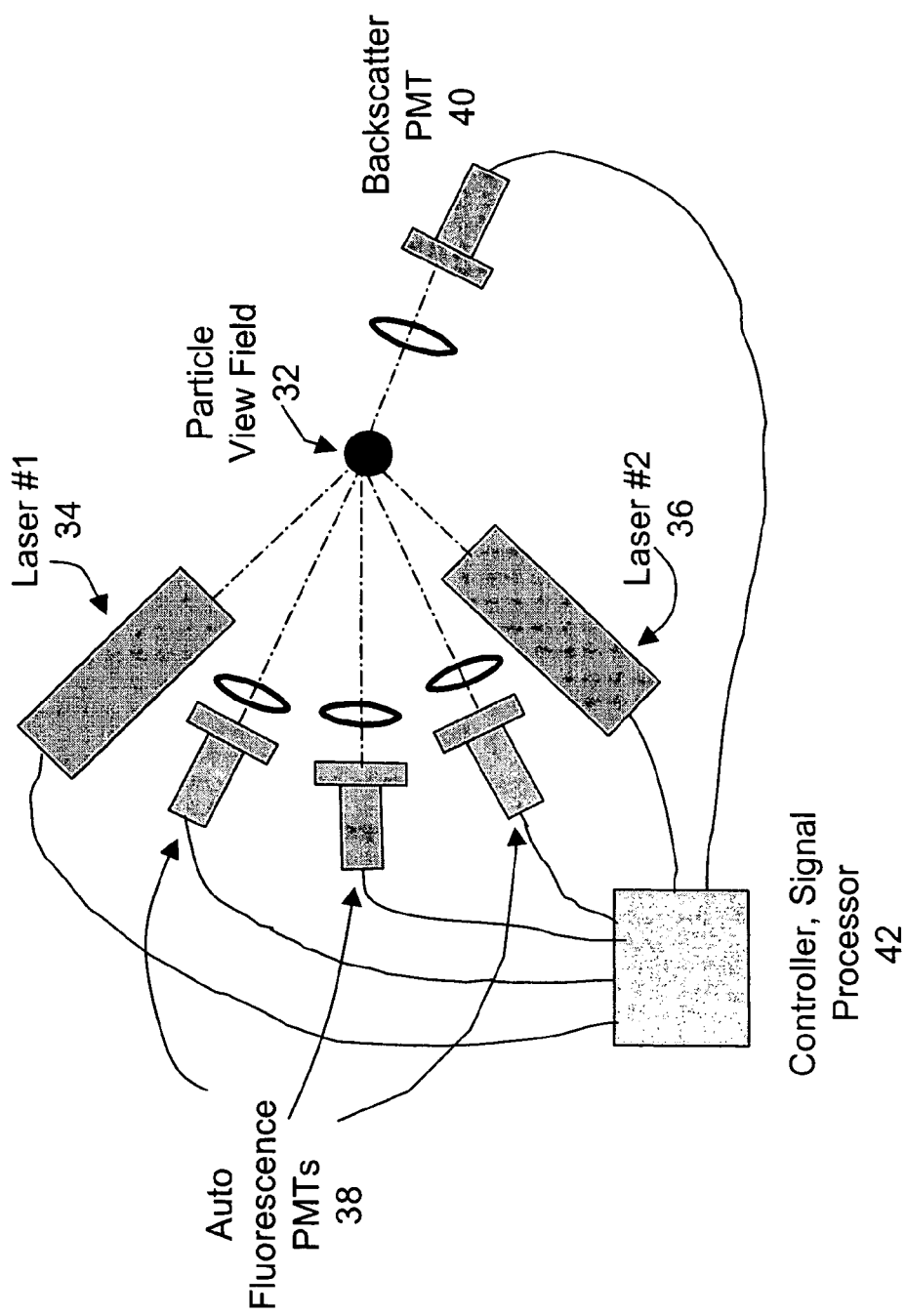
FIG. 3 is a diagrammatic view of a multi-spectral UV Detection System.
Figure 4:
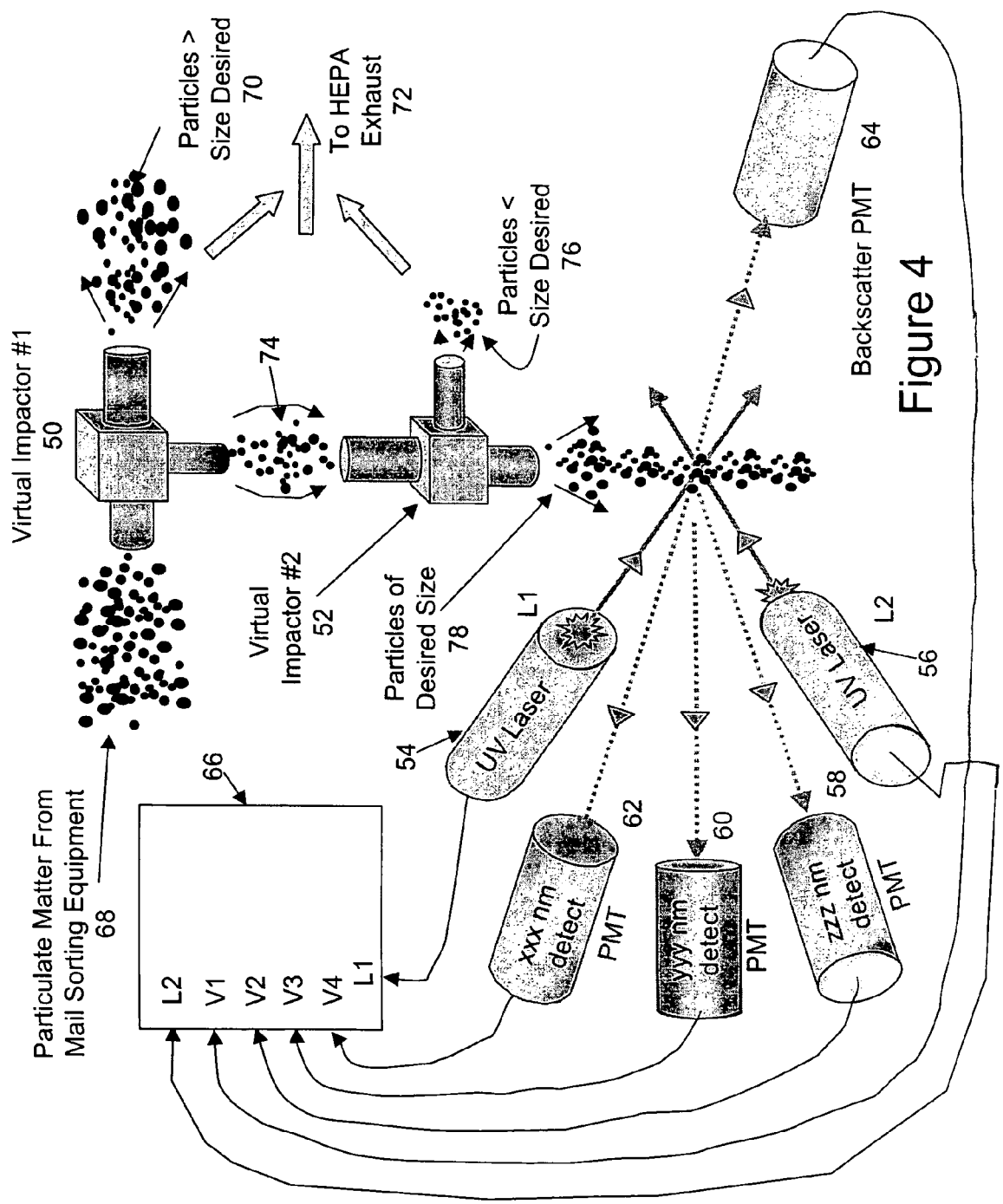
FIG. 4 shows more details of the system for detecting particulate matter from the mail sorting equipment.

FIG. 1 shows a schematic view of a mail sorting/handling line into which the present invention has been incorporated. The mail is unloaded onto the feed section 12 of the conveyor system and travels in the direction of arrow 14. At a chosen trigger location 16, various predetermined trigger data are sensed by various sensors, depending upon the particular data chosen for causing a triggering of the system.

In one embodiment of the invention, the trigger data are collected relative to the number of particles detected over a defined time interval, one second, for example, that meet certain criteria corresponding to a "region of threat" or ROT. These criteria are typically related to the size and fluorescence characteristics of the particle. Weapons grade biohazard particulates are targeted for the respirable size range, which is of 1-10 microns in diameter. Certain fluorescence characteristics are indicative of biological activity.

Further downstream of the trigger location 16 is an advanced facer canceller system (AFCS) 17 an image scanning station 18 at which the outside of the mail is scanned.

Box 20 shows a representation of the trigger data on a time-magnitude graph, and box 22 shows the different types of scanned images which would be obtained by the scanner. FIG. 2 shows the box 20 on a greater scale showing the time line 24, the magnitude scale 26 indicating ROT counts and two trigger alarm events 28 and 30.

The trigger system counts the number of particles that meet the ROT criteria over a one second interval. Referring to FIG. 2, the numbers on the vertical axis, 26, indicate the number of particles counted over a one second interval that meet the ROT criteria. The horizontal axis is the time of day. If this count exceeds a predefined, experimentally determined, alarm level, 31, as shown by events 28 and 30, then an alarm condition exists.

FIG. 3 shows a multi-spectral UV laser induced fluorescence (UVLIF) trigger system which has a particle view field 32, a first laser 34, a second laser 36, photo multiplier tubes (PMTs) 38 for detecting autofluorescence, a PMT 40 for detecting backscatter signals and a signal-processor/controller 42. Lasers 34, 36 operating in the UV band, are trained on the particles moving through the view field to induce an autofluorescent response. The PMTs, 38 capture the intensity of any response induced. PMT 40 measures the particle's backscatter which is used to determine particle size. The control system manages the lasers and processes the signals captured by the PMTs.

FIG. 4 shows a more detailed view of the UV-LIF trigger system which includes a first virtual impactor 50, a second virtual impactor 52, in addition to UV lasers 54 and 56, three PMT detectors—for detecting particle autofluorescence, and a backscatter PMT 64, all of which feed into a control system 66 for analysis.

As shown the particulate matter 68 from the mail sorting equipment is fed into the first virtual impactor 50 and particles 70 which are greater than the size desired are withdrawn to be exhausted through a HEPA filter 72. The particles 74 which are not withdrawn during this step are sent to the second virtual impactor 52 where particles 76 which are less than the desired size are withdrawn and sent to the HEPA filer 72 to be exhausted from the system. The remaining particles 78, which are roughly of the desired size are sent to the particle view field 32 as shown in FIG. 3 and detection of the particulate matter is conducted.

Referring to FIG. 4, lasers operating at the appropriate frequencies are focused on the particles. Depending on the particle constituents, the laser light will be absorbed, which will result in the autofluorescence of the particle at a wavelength characteristic of biological activity—if said activity is present. The PMTs are filtered to be sensitive to the desired autofluorescence activity. In addition to autofluorescence, the laser light hitting the particle causes a backscatter signal to be generated. The backscatter signal can be processed to determine the size of the particle. Coincidence of size and autofluorescence criteria within specific ranges indicates the particle may be a biohazard.

At the end of the conveyor line the mail may be sorted into a bin reserved for suspect mail pieces which may then be further examined either at the immediate location or be removed to an isolated location in a room with a protected air circulation system or the like to prevent spreading of the hazardous material.

An image of each mail piece is scanned when processed by the AFCS. A trigger system is implemented at first pinch point on the AFCS after the dual pass fine cull (testing is done in Baltimore, Binghamton). The trigger system monitors the air at the first pinch point (point at which the first pair of pinch rolls act on the mail piece, which causes expelling of air and particulate matter inside the mail piece). If a possible event is detected by the trigger, the images of the suspect mail pieces will be captured and analyzed.

The image technology provides for obtaining images which provide information indicative of mail which is more likely to be from suspicious sources and provide increased risk factors such as the following:

a. Excessive postage;
b. Badly typed or hand written address;
c. Hand written characters are printed rather than script;
d. Typed address has uneven background of different color/shade (cut from other paper);
e. Misspelled words in address;
f. Addressed without any indicated name;
g. Excessive tape or discoloration evident in mail piece image;
h. No return address present;
i. Return address does not match postmark;
j. Return address is from a suspect area or interest; and
k. Various restrictive legends, such as: "Personal", "To be Opened Only by Addressee", "Special Delivery", "Open Immediately" and the like.
l. Actual addresses of well known persons, such as Congressmen.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

The invention claimed is:

1. Apparatus for detecting hazardous particulates in a mail stream, comprising:

A. means for detecting hazardous particulates in or on mail pieces in a mail stream;
B. a scanner for scanning each mail piece wrapper to form an image thereof;
C. means for evaluating the image based upon predetermined events and determining the probability of the mail piece being suspect; and
D. combing the results of the detecting means and the evaluating means to determine the level of probability of the mail containing hazardous material;

wherein the evaluating means uses the following factors:

a. Excessive postage;
b. Badly typed or hand written address;
c. Hand written characters are printed rather than script;
d. Typed address has uneven background of different color/shade (cut from other paper);
e. Misspelled words in address;
f. Addressed without any indicated name;
g. Excessive tape or discoloration evident in mail piece image;
h. No return address present;
i. Return address does not match postmark; and
j. Return address is from a suspect area or interest.

2. Apparatus as defined in claim 1 wherein the detecting means is an aerosol trigger for generating a signal which provides trigger data about the hazardous particulate detected.

3. Apparatus as defined in claim 2 wherein the trigger data is collected relative to the amount of particles detected over a defined time interval and predetermined criteria are provided corresponding to a region of threat, such criteria being related to the size and fluorescence characteristics of the particulate.

4. Apparatus as defined in claim 3 wherein the detecting means includes the detection of weapons grade biohazard particulates in the respirable size range of 1-10 microns in diameter.

5. Apparatus as defined in claim 2 wherein the trigger includes a multi-spectral UV laser induced fluorescence trigger system having a particle view field, a first laser, a second laser, photo multiplier tubes for detecting auto-fluorescence, at least one photo multiplier tube for detecting backscatter signals and a signal-processor/controller.

6. Apparatus as defined in claim 5 where the lasers operate in the UV band and are trained on the particles moving through The view field to induce an auto-fluorescent response and the PMTs capture The intensity of any response induced.

7. Apparatus as defined in claim 6 wherein depending upon The particle constituents the laser light will be absorbed resulting in the auto-fluorescence of the particle at a wavelength characteristic of biological activity.

8. Apparatus as defined in claim 7 wherein the photo multiplier tubes are filtered to be sensitive to the desired auto-fluorescence activity.

9. Apparatus as defined in claim 8 wherein laser light hitting the particle causes a backscatter signal to be generated, which signal is processed to determine the size of The particle.

10. Apparatus as defined in claim 9 wherein coincidence of size and auto-fluorescence criteria within specific ranges indicates the particulate may be a biohazard.

11. Apparatus as defined in claim 2 wherein the trigger includes first virtual impactor where particles which are greater than a desired size are withdrawn and exhausted through a HEPA filter to be exhausted from The system and a second virtual impactor to which particles which are not greater than a desired size are delivered and where particles which are less than a predetermined desired size are withdrawn and sent to the HEPA filter to be exhausted from the system and the remaining particles which are roughly of the desired size are sent to the particle view field and detection of the particulate matter is conducted.

12. Apparatus as defined in claim 2 where the trigger is located at the first pinch point on the system.

13. Apparatus as defined in claim 1 wherein the scanner is downstream of the detecting means and is an advanced facer canceller system at an image scanning station at which the outside of the mail is scanned.

14. Apparatus as defined in claim 1, wherein each factor is provided with a rating and the ratings are averaged to determine the overall suspect nature of the image.

15. Apparatus as defined in claim 1 comprising means for diverting mail having a high probability of containing hazardous material into a repository separate from other mail.

16. Apparatus as defined in claim 1 wherein the factors used by the evaluating means also includes:

k. Various restrictive legends, including “Personal”, “To be Opened Only by Addressee”, “Special Delivery”, “Open Immediately” and the like.

17. A method for detecting hazardous particulates in a mail stream, comprising the steps of:

A. detecting hazardous particulates in or on mail in the mail stream;

B. forming an image of each of the mail piece wrappers and determining the probable suspect nature of the mail based upon a predetermined set of characteristics; and C. combining the data from steps A. and B. to form a conclusion as to the probability of the mail containing hazardous material;

wherein the probable suspect nature of the mail is based upon the following factors:

l. Excessive postage;

m. Badly typed or hand written address;

n. Hand written characters are printed rather than script;

o. Typed address has uneven background of different color/shade (cut from other paper);

p. Misspelled words in address;

q. Addressed without any indicated name;

r. Excessive tape or discoloration evident in mail piece image;

s. No return address present;

t. Return address does not match postmark; and u. Return address is from a suspect area or interest.

18. A method as defined in claim 17 wherein each factor is provided with a rating and the ratings are averaged to determine the overall suspect nature of the image.

19. A method as defined in claim 17 further comprising the step of diverting mail having a high probability of containing hazardous material into a repository separate from other mail.

20. A method as defined in claim 17 wherein the factors used by the evaluating means also includes:

k. Various restrictive legends, including “Personal”, “To be Opened Only by Addressee”, “Special Delivery”, “Open Immediately” and the like.

* * * * *

UNITED STATES PATENT AND TRADEMARK OFFICE
CERTIFICATE OF CORRECTION

| | |
|---|---|
| PATENT NO. | : 7,356,163 B2 |
| APPLICATION NO. | : 10/865063 |
| DATED | : April 8, 2008 |
| INVENTOR(S) | : John T. Beckert et al. |

It is certified that error appears in the above-identified patent and that said Letters Patent is hereby corrected as shown below:

Column 8, line 16 (Claim 17), the portion of the line reading "detecting hazardous particulates in" should read --detecting harzardous particulates present in--

Signed and Sealed this

Fifth Day of August, 2008

JON W. DUDAS
*Director of the United States Patent and Trademark Office*